(12) United States Patent
Rogachefsky et al.

(10) Patent No.: US 9,227,080 B2
(45) Date of Patent: Jan. 5, 2016

(54) APPLICABLE DEVICE FOR HEALING INJURIES WITH MAGNETIC FIELDS

(71) Applicant: Richard A. Rogachefsky, San Pedro, CA (US)

(72) Inventors: Richard A. Rogachefsky, San Pedro, CA (US); James Seal, Boca Raton, FL (US)

(73) Assignee: Richard A. Rogachefsky, San Pedro, CA (US)

( * ) Notice: Subject to any disclaimer, the term of this patent is extended or adjusted under 35 U.S.C. 154(b) by 0 days.

(21) Appl. No.: 14/547,307

(22) Filed: Nov. 19, 2014

(65) Prior Publication Data

US 2015/0073201 A1    Mar. 12, 2015

Related U.S. Application Data

(63) Continuation of application No. 13/485,811, filed on May 31, 2012, now abandoned.

(51) Int. Cl.
*A61N 1/00*    (2006.01)
*A61N 2/12*    (2006.01)
*A61N 2/00*    (2006.01)

(52) U.S. Cl.
CPC .. *A61N 2/12* (2013.01); *A61N 2/00* (2013.01); *A61N 2/004* (2013.01); *A61N 2/008* (2013.01)

(58) Field of Classification Search
CPC ......... A61N 2/02; A61N 2/006; A61N 2/004; A61N 2/008; A61N 2/06; A61N 2/12; A61N 2/00; A61N 1/36021; A61N 1/36025; A61N 1/326; A61N 1/0492; A61N 1/08
USPC ............................ 600/9, 13–15; 128/897–899
See application file for complete search history.

(56) References Cited

U.S. PATENT DOCUMENTS

| | | | | |
|---|---|---|---|---|
| 4,266,532 | A * | 5/1981 | Ryaby et al. | 600/14 |
| 4,587,956 | A * | 5/1986 | Griffin et al. | 600/15 |
| 4,942,884 | A | 7/1990 | Ichinomiya et al. | |
| 5,518,495 | A * | 5/1996 | Kolt | 600/13 |
| 5,720,046 | A * | 2/1998 | Lopez et al. | 2/159 |
| 5,782,743 | A * | 7/1998 | Russell | 600/9 |
| 6,146,324 | A * | 11/2000 | Engel | 600/15 |
| 6,317,630 | B1 | 11/2001 | Gross et al. | |
| 6,344,021 | B1 | 2/2002 | Juster et al. | |
| 2003/0158585 | A1 * | 8/2003 | Burnett | 607/2 |
| 2004/0176805 | A1 | 9/2004 | Whelan et al. | |

(Continued)

FOREIGN PATENT DOCUMENTS

DE        19963908 A1 *  7/2001

OTHER PUBLICATIONS

Markov: "Biological Windows": A Tribute to W. Ross Adey The Environmentalist 25, p. 67-74, 2005 2005 Springer Science + Business Media, Inc.

(Continued)

*Primary Examiner* — Navin Natnithithadha
*Assistant Examiner* — Sunita Reddy
(74) *Attorney, Agent, or Firm* — Andrew J. Anderson, Esq.; Harter Secrest & Emery LLP

(57) ABSTRACT

A medical device includes a substrate, a magnetic field emitter disposed on a side of the substrate, and an adhesive on the side of the substrate opposite the emitter.

17 Claims, 11 Drawing Sheets

(56) References Cited

U.S. PATENT DOCUMENTS

| | | |
|---|---|---|
| 2005/0288744 A1* | 12/2005 | Pilla et al. .................. 607/86 |
| 2008/0051621 A1* | 2/2008 | Vines et al. .................. 600/15 |
| 2009/0082610 A1 | 3/2009 | Wolf et al. |
| 2010/0222631 A1 | 9/2010 | Pilla |
| 2011/0112352 A1 | 5/2011 | Pilla et al. |
| 2011/0130618 A1 | 6/2011 | Ron Edoute et al. |
| 2011/0207989 A1 | 8/2011 | Pilla et al. |
| 2011/0213195 A1 | 9/2011 | Kraus et al. |
| 2011/0218381 A1 | 9/2011 | Ruohonen |
| 2011/0230943 A1 | 9/2011 | Johnson et al. |
| 2012/0302821 A1* | 11/2012 | Burnett .................. 600/14 |
| 2015/0080636 A1 | 3/2015 | Rogachefsky et al. |

OTHER PUBLICATIONS

PCT—International Search Report, mailed Sep. 5, 2013 in corresponding PCT International Application No. PCT/US2013/042870 (4 pages).

PCT—Written Opinion of the International Searching Authority, mailed Sep. 5, 2013 in corresponding PCT International Application No. PCT/US2013/042870 (9 pages).

* cited by examiner

APPLICABLE DEVICE FOR HEALING INJURIES WITH MAGNETIC FIELDS

CROSS-REFERENCE TO RELATED APPLICATIONS

This application is a continuation of and claims priority to, copending application U.S. Ser. No. 13/485,811, filed May 31, 2012, the disclosure of which is incorporated by reference herein in its entirety.

FIELD OF THE INVENTION

The disclosure relates to magnetic field therapy. More particularly this disclosure relates to a device for generating selected magnetic or electromagnetic fields with defined parameters that is designed for placement proximate a user's injury site to promote healing at that site.

RELATED ART

Electromagnetic fields have been proposed for therapeutic purposes for many years. An important feature of magnetic/electromagnetic stimulation is that electric and magnetic field components behave differently. When an electric field reaches a conductive surface, it is converted into an electrical current along the surface. Conversely, many materials are wholly or partly transparent to the magnetic field, allowing the magnetic field to penetrate deep into the body. The depth of penetration is dependent on the technique used to generate the magnetic field and the nature of the tissue penetrated.

Magnetic and electromagnetic field stimulation accelerates the healing processes. It is now clear that endogenous electromagnetic and magnetic interactions are associated with many basic physiological processes on a cellular level ranging from ion binding and molecular conformation in the cell membrane to macroscopic alterations in tissues.

At present, 27.12 MHz signals have been approved by the FDA for the treatment of pain and edema in superficial soft tissues. This frequency signal has been applied to surgical sites post-operatively via "drum" applicator or circular coil to augment wound healing post surgery for such cases as breast augmentation or reduction.

Fields have been generated externally by signal generators connected to bulky coils oriented so that the electromagnetic fields pass through the soft tissue or bone to be treated. These systems, while effective, have the disadvantage that they require bulky signal generating apparatus and electromagnetic field generating coils to be situated near a patient's wound to apply a field to the wound. This is a particular problem for patients who are ambulatory because the signal generators and coils are not easily portable, and a lesser but still significant problem for patients confined to a bed because the apparatus is bulky.

SUMMARY OF THE INVENTION

The present disclosure remedies the foregoing shortcomings of the prior art by providing an improved, non-cumbersome, compact, medical device that promotes wound and/or bone healing by application of magnetic or electromagnetic fields close to a patient's injury site.

In one aspect of the invention, a device includes a substrate, an electromagnetic field emitter disposed on a side of the substrate, and an adhesive on the side of the substrate opposite the emitter.

An understanding of these and other aspects, features, and benefits of the invention may be had with reference to the attached figures and following disclosure, in which preferred but not limiting embodiments of the invention are illustrated and described.

BRIEF DESCRIPTION OF THE DRAWING FIGURES

DETAILED DESCRIPTION OF PREFERRED EMBODIMENTS OF THE INVENTION

The invention relates to healing devices that are applied to a user's skin proximate an injury site for assisting in wound healing, treating infection, reducing pain, treating fractures, and for other therapeutic purposes. Preferred embodiments of the invention will be described with reference to the figures.

Figure 1:
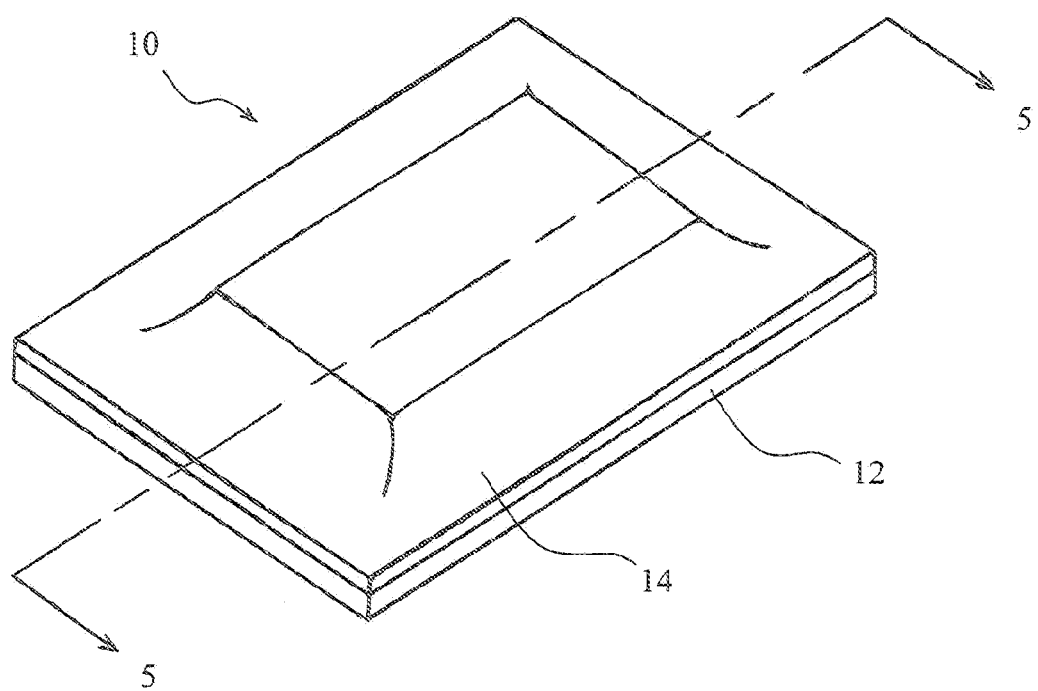
FIG. 1 is a perspective view of a wearable wound healing device according to a first embodiment of the disclosure.

FIG. 1 shows a wearable device 10 according to a first embodiment of the invention. As used herein, the term wearable generally means capable of being placed on a person, and which will remain on the person for some period of time, usually including periods when the person is ambulatory. The device generally includes a substantially planar substrate 12, a top cover 14 disposed over the substrate 12, and an adhesive 16 on a bottom surface of the substrate, see FIG. 3, opposite the top cover 14. A user wears the device 10 by applying the adhesive coated surface to the user's skin, much like a conventional adhesive bandage. The device 10 is illustrated as being substantially rectangular, but this shape is not required. As will be appreciated from the following description, the device may be any shape, and is preferably sized and shaped to maximize coverage and exposure of an injury to be treated with the device.

The substrate 12 and the top cover 14 preferably are medical-grade, sterile substrates suitable for contacting a user's skin without adverse effect. As used herein, a substrate may be any material preferably, but not necessarily in sheet form, that can be placed in contact with or near the skin. The substrate and cover are flexible or pliable so as to generally minimize impediment to the user's normal movement when the device is adhered to the user's in-tact skin around the wound or injury site. They may be made from any number of commercially available materials, such as cloth, nylon, polymers, and combinations thereof, for example. Regardless of the material used, in a preferred embodiment the substrate is sufficiently strong to carry the components of the invention, as will be described in more detail below. In some embodiments, the substrate and top cover preferably are waterproof, such that water or other liquids will not migrate there through.

The top cover 14 and the substrate 12 encapsulate components, as will be described in more detail below with reference to FIG. 2. Thus, the top cover 14 and substrate 12 form and define a compartment. In a preferred embodiment, this compartment is sealed about substantially its entire periphery to maintain the components within the compartment and to discourage a user from accessing the components disposed therein. In other embodiments, though, a compartment may be accessible, e.g., to repair or update components contained in the compartment replace a battery, or the like. As noted above, the substrate 12 and the top cover 14 may be impervious to water, such that components in the compartment will not be contacted by water. The compartment may be formed by affixing the top cover to the substrate in any known manner, including, but not limited to, adhering with adhesives or welding using known techniques, such as ultrasonic welding. The top cover 14 and the substrate 12 preferably completely encapsulate the components contained in the compartment.

Figure 2:
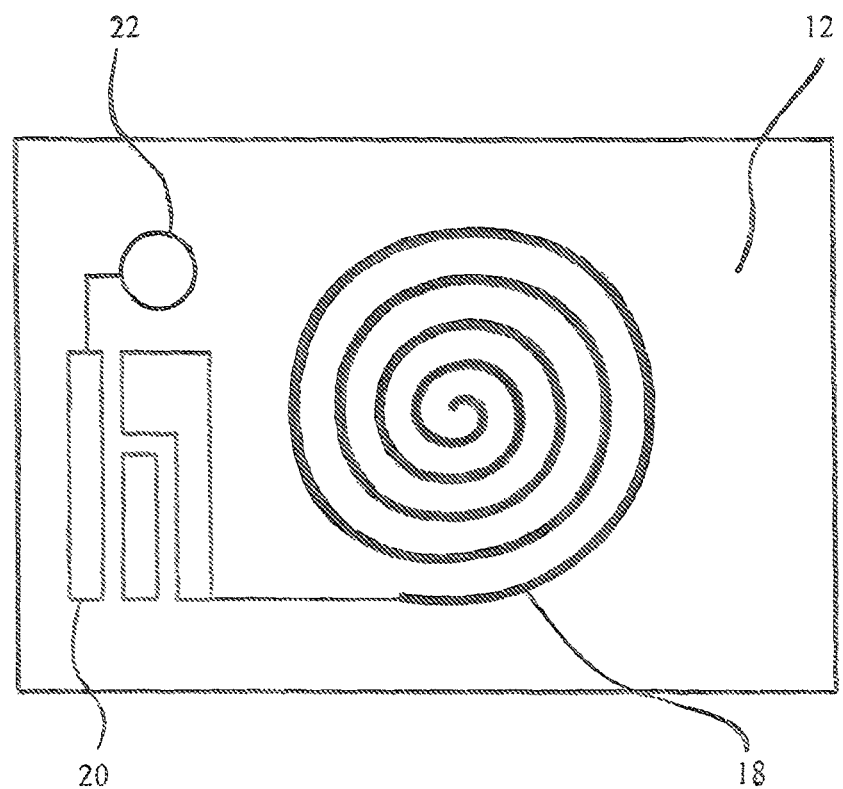
FIG. 2 is a perspective view of the device of FIG. 1 in which a top cover of the device has been removed.

FIG. 2 illustrates an example of the components encapsulated between the top cover 14 and the substrate 12. In that figure, the top cover 14 is removed to illustrate an electromagnetic field emitter 18 disposed on the substrate. The electromagnetic field emitter 18 is in the form of a coil of wire or other conductive material and may take any conventional shape and form, including an electromagnetic coil such as a helical or spiral coil or multilayer wound coil through which a current is passed to create a magnetic field. The illustrated emitter 18 is a conventionally known "pancake-type" coil. The coil may be formed by winding a wire, such as a copper wire, on the substrate 12. Or, in a preferred embodiment, the coil is formed in the way a printed circuit is formed, for example by depositing a metal, such as copper, onto the substrate to form a coil using known deposition, including known masking and/or etching, techniques. The deposited coil may be a single-layer coil as illustrated or may include turns in multiple insulated layers. That is, deposited pancake coils may be stacked one on top of the next. In such a configuration, an intermediate layer, such as an insulating layer, may also be provided between stacked coil layers. The stacked coils are connected to each other in series or parallel, or a combination thereof, to form a continuous current path. Such an arrangement will provide an increased number of turns for the coil, and thus a stronger field, for example, to penetrate tissue more deeply, but still provide a relatively low profile. It is generally contemplated that a single coil will be needed, but the stack of coils just described could be provided when, for example, a stronger field is desired for deeper penetration into the body, especially for deep tissue wounds or bone healing.

Although in the embodiment illustrated in FIG. 2 the coil is significantly smaller than the footprint of the compartment, to allow for other components to be disposed on the substrate, such is not necessary. For example, the coil may very closely approximate the size of the footprint of the compartment, to increase the area of the field within the confines of the device, e.g., to ensure that the entire wound is exposed to the field. In such an embodiment, the additional components, which will be described below, could be stacked on top of the coil, instead of on the substrates, or within the coil for example.

A controller 20, which preferably is fabricated on a printed circuit board, preferably a flexible printed circuit board, and/or as an integrated circuit is connected to the coil of the electromagnetic field emitter 18. The controller, or signal generator 20 generates a signal to energize the electromagnetic field emitter 18. The controller 20 may also be formed on the substrate using deposition techniques known in the art. Alternatively, the controller 20 may be formed separately and placed on the substrate 12. It may be fixed to the substrate, for example, using an adhesive such as epoxy or the like. Also illustrated in FIG. 2 is a power source 22. In the figure, the power source 22 is a battery. The battery is in communication with the electromagnetic field emitter 18 and the controller 20. The battery is preferably connected to the electromagnetic field emitter 18 and the controller 20 with leads. The leads may be deposited on the substrate as with the controller and/or the coil or they may be embodied as wires connecting the components. Generally speaking, the controller is energized by the power source to generate a signal that, when applied to the electromagnetic field emitter, creates an electromagnetic field. The battery may be connected to the controller which is connected to the electromagnetic field emitter.

In one embodiment, the battery is connected to the controller to provide power to the controller 20. In turn, the controller is connected to the electromagnetic field emitter. The controller is programmed with a series of instructions for applying a modulated current to the electromagnetic field emitter 18. The controller may be programmed with a routine such as a series of intensity and/or time dependent instructions. Depending upon the program routine, the controller will modulate the power from the power source such that a controlled current is supplied to the electromagnetic field emitter 18, which in turn will create an electromagnetic field in response to the applied current. By varying the current and the time, any number of therapeutic routines may be used.

The controller may also be preprogrammed with a number of routines for application of different electromagnetic fields to the injury site. For example, routines may be included that depend upon the location and/or severity of a wound to injured tissue to be treated. Distinct fields also may be provided for the three general phases of wound healing, i.e., inflammatory, proliferative, and remodeling. In still other embodiments, the controller may be programmable either before application to the patient, or after being applied. A lead may be accessible through the top cover 14 or the substrate 12 to allow temporary tethering to a computer or the like useable in programming the controller 20. In a preferred embodiment, though, the controller will include a wireless receiver configured to receive programming instructions from a computer or the like equipped with a transmitter. The controller may also include a wireless transmitter for transmitting data corresponding to the signal generated by the controller.

Although FIG. 2 contemplates inclusion of the controller and the power source between the substrate 12 and the top cover 14, in other embodiments of the invention, all or a portion of the controller and/or the power source may be outside the device 10. For example, the device may be powered inductively. In such a scenario, a field generator disposed outside the device emits an electromagnetic field, which, when placed in proximity to an induction coil disposed in the device 10, will transfer energy capable of charging the battery. A separate coil may be provided as the induction coil, or in one embodiment, the coil used as the electromagnetic field emitter may be used as the induction coil. In one embodiment of this induction charge scenario, the external generator emits a field that may be different from the field generated by the electromagnetic field emitter, i.e., so it will not adversely affect the healing sought to be accomplished by the electromagnetic field emitter. In another embodiment, the field emitted by the external generator may closely approximate the "healing" field. In this embodiment, the generator may be used when the device is not worn, such that the charging field does not interfere with the healing field, although the charging field could be applied when the device is worn, in which case the charging field may also help promote healing, i.e., because the induction coil may not completely absorb the field and that portion of the field that is not absorbed will be applied to the injury.

Figure 3:
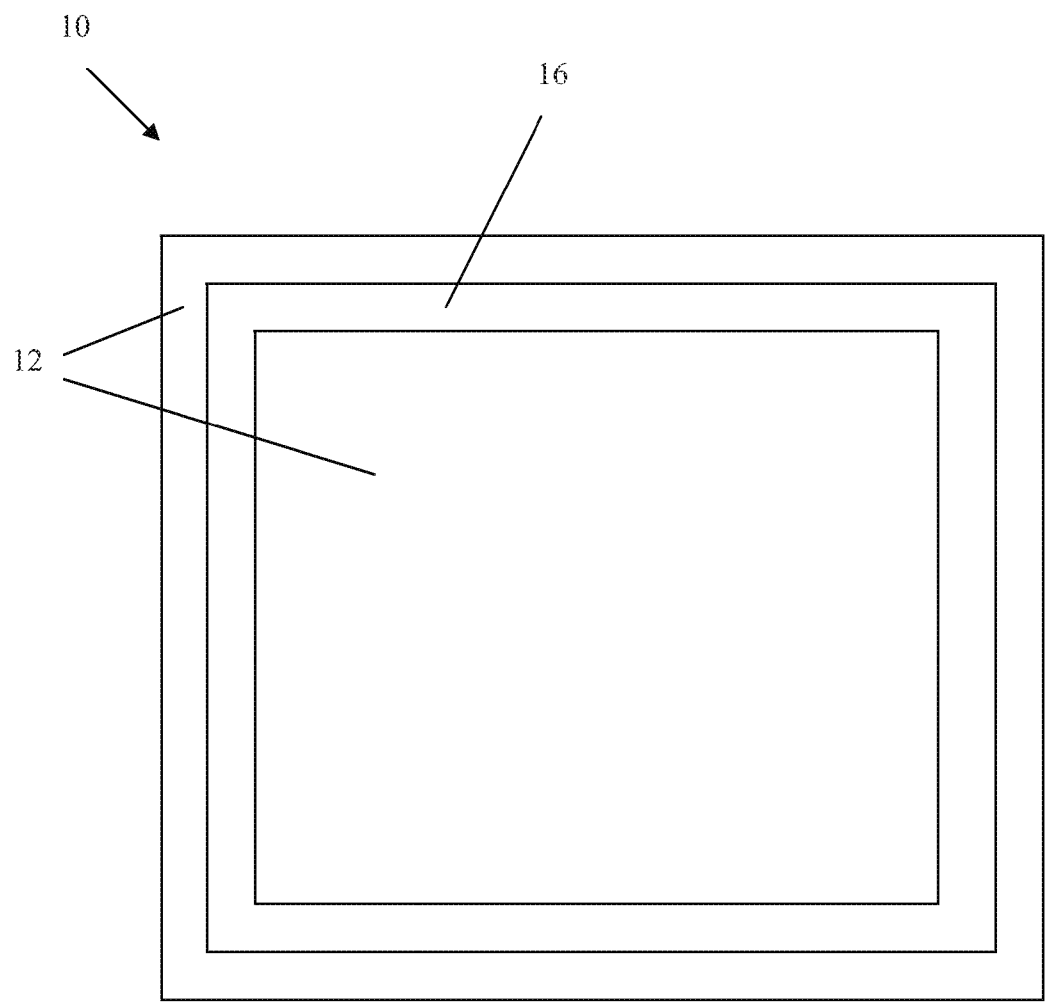
FIG. 3 is a bottom plan view of the device of FIG. 1.

FIG. 3 is a bottom view of the device 10 of FIG. 1. This figure shows the pattern of adhesive layer 16. Specifically, the adhesive layer 16 is disposed in a substantially constant thickness layer about the periphery of the device 10, for example, to circumscribe the periphery. In use, the adhesive layer 16 having the shape illustrated in FIG. 3 is applied to the epidermis to circumscribe the wound-to-be-treated, to position the emitter proximate the injury. The adhesive may be any medical-grade adhesive, including an adhesive used in conventional adhesive bandages, such as those sold by Johnson & Johnson under the BAND-AID trademark. The adhesive may be chosen to promote relatively pain-free removal of the device. For example, an adhesive may be chosen that weakens or breaks down over the time in which the device is intended to be worn. Alternatively, the adhesive may be dissolvable when contacted by a non-toxic solvent. To this end, a port or other opening may be provided through the layers above the adhesive, such that the solvent can be applied directly to the adhesive.

In one embodiment of the invention such as would be used to treat an open wound or a cut, the adhesive layer 16 will completely surround the periphery of the substrate and adhere to the intact skin around the wound. The portion of the substrate inside the adhesive layer is approximated over the wound. Although not illustrated, a removable backing may be provided on the adhesive until the device is applied, to cover the adhesive.

The device 10 as illustrated is designed for achieving close proximity between the field generating coils and the injury, which may be a fracture or an open wound. Specifically, the device 10 is applied to the skin such that the adhesive 16 surrounds the wound to be treated, leaving the portion of the substrate bounded by the adhesive in close proximity with, and in some embodiments, touching, the wound. To this end, the portion of the substrate bounded by the adhesive 16 is preferably sterile. When the adhesive is contiguous, as in FIG. 3, it may act to "seal" the wound, i.e., to ensure that no contaminants or the like find their way under the device and onto the injury site. Using a sterile substrate will further ensure that this sealing effect of the wound will keep the wound clean. In other embodiments, a contiguous adhesive layer that seals the wound upon application of the device to the skin is not required. Other patterns of adhesive, including discrete "spots" or "regions" of adhesive may be provided instead of the illustrated continuous adhesive area. When the substrate may contact the injured tissue, for example, if the injury is an open wound or sore, it may be generally desirable to maintain the portion of the substrate that could contact the injury or wound site free from adhesive, such that the adhesive does not adhere to the injury. Conversely, when the injury is below the skin level and the epidermis is intact, such as with some fractures or sprains, any or all of the entire substrate may be covered with an adhesive. In the foregoing examples, it is preferable that the adhesive only adhere to skin that is intact. As noted above, in some applications, the substrate and the top cover are air permeable, allowing the injury to "breath."

Figure 4:
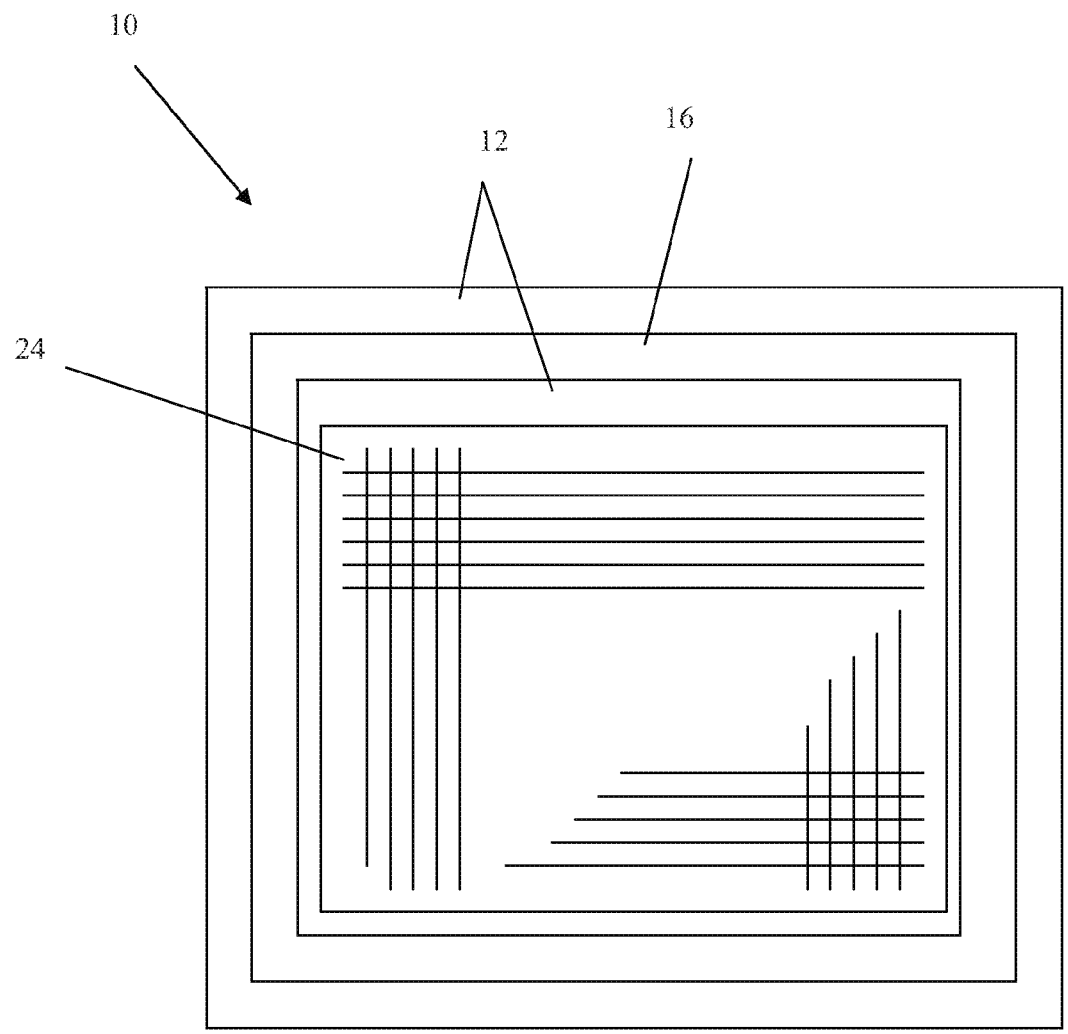
FIG. 4 is a bottom, plan view of the device of FIG. 1 according to another embodiment of the invention.

In FIG. 3, the area of the bottom of the substrate 12 not covered by adhesive is merely exposed substrate. Because this portion may contact a wound, it is preferably sterile and non-irritating. In other applications, for example, where weeping or bleeding from the injury may occur, a sterile, absorbent material may be provided on the portion of the bottom of the substrate upon which adhesive is not disposed. FIG. 4 shows such an embodiment where a pad 24 is provided on the bottom of the substrate for contacting the wound. The pad 24 is preferably any known, commercially available material, such as gauze, that will absorb fluid and protect the wound. As is well known in the art, the pad 24 may carry a salve or ointment to aid in healing the wound.

While FIG. 4 offers provisions for a specialized material that is particularly suitable for contacting a wound, for example, to provide a therapeutic benefit, in other embodiments a spacer or the like may be provided that distances the substrate from the skin. That is, in some embodiments it is preferred that the device does not contact the wound or injured tissue at all. By providing the spacer the substrate is raised off the wound, but the emitter is still carried directly above the wound for exposure of the wound to the electromagnetic field. Preferably, the spacer is provided at the periphery of the device, such as between the adhesive and the substrate so as to keep the portion of the substrate proximate the injured tissue.

Figure 5:
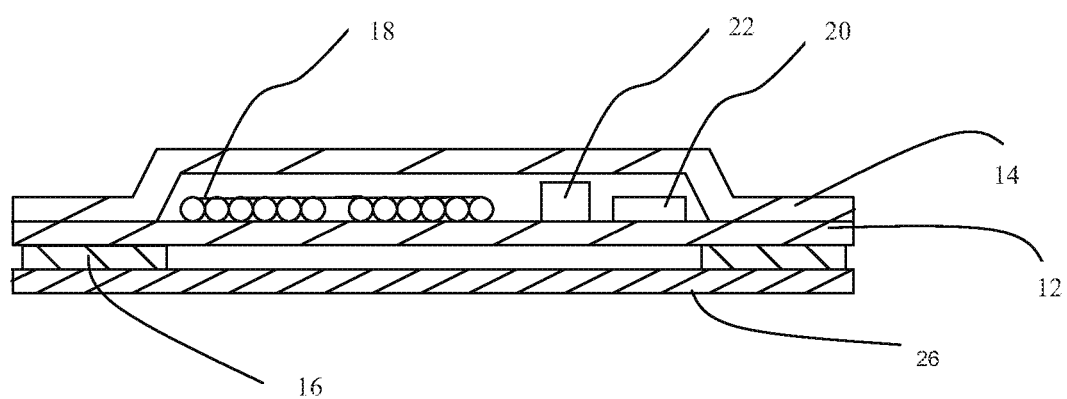
FIG. 5 is a cross-sectional view of the device of FIG. 1, taken along section line 5-5 in FIG. 1.

The electromagnetic field emitter generally is a structure having conventional functioning that will create an electromagnetic field at a frequency of up to about 120 Hz. While the research is ongoing, there is some evidence that a frequency of 15.6 may be advantageous for some types of injuries. In various embodiments, the magnetic field emitter may emit a field of less than about 120 Hz, less than about 60 Hz, less than about 30 Hz, less than about 15 Hz, or less than about 5 Hz. While 120 Hz is thought to be a useful upper limit, the invention is not so limited. Higher frequencies may be advantageous with smaller field generating coils, and the invention is not intended to be limited to any specific frequency. The field is also characterized by being less than about 1000 Gauss. There is some evidence that there are therapeutically effective ranges at 5-10 G., 150-200 G., and 450-500 G. Those ranges are specifically contemplated in accordance with the invention, but are not limiting. Higher and lower strengths are also intended to be included. In various embodiments, the magnetic field emitter may emit a field of less than about 1000 Gauss, less than about 500 Gauss, less than about 250 Gauss, less than about 100 Gauss, less than about 50 Gauss, or less than about 10 Gauss. As will be described in more detail below, the emitter can be placed in close proximity to an injury, such as a lesion, a sprain, a bone fracture, or muscle or tissue affliction. Although only one emitter is illustrated in FIG. 2, more emitters may be provided. In the embodiment illustrated in FIG. 3 (and as is also shown in FIG. 5) the emitter preferably is disposed in the footprint of the device 10 in the area inside the adhesive layer. The coils comprising the emitter preferably are maximized in size to fill as much of this portion of the footprint as possible, to create the maximum-strength field possible. This configuration also allows for easy location of the emitter relative to the wound. The emitter should be placed directly adjacent the injury. When a user applies the device by placing the adhesive around the injury, the emitter is in a preferred position relative the injury to provide maximum effect. That is, the emitter is positioned such that the injury to be healed, such as an open wound, sore, or fracture, is disposed in the electromagnetic field. Preferably, the high flux portion of the field intersects the injury. This close positioning allows for a lower power requirement.

As will be appreciated by those of ordinary skill in the art, known electromagnetic field emitters produce electromagnetic fields having a predictable size and shape and can be manipulated to have desired field parameters. For example, the wave may be a, half wave, full wave or the like. The wave shape may be sinusoidal, square, triangular, or any other suitable shape. In one embodiment, the wave may be a rectified sinusoidal wave producing alternating current half cycles occurring at a frequency of from about 50 to about 100 cycles per second. In another embodiment, full wave rectified alternating current half cycles occur at a frequency of up to about 100 cycles per second, more preferably up to about 50 cycles per second, and still more preferably up to about 10 cycles per second. The electromagnetic signal may also represent a set of pulses, such as bipolar, unipolar, trapezoid, or triangular pulses, for example. The pulses preferably are repeated, for example, up to 10 times per second to form a treatment modality. As described above, the field may be changed to achieve different results, for example, for optimization for different stages of healing. It also may be desirable to vary the frequency and strength of the field, for example, depending upon the wound to be treated. Treating a fracture will require a stronger, e.g., deeper penetrating, field than treatment of a lesion or other superficial soft tissue wound. Moreover, the changes in field characteristics may be provided according to a predetermined schedule or regimen, or may be manually changed by a doctor or technician. FIG. 2 shows a pancake-type coil, but helical coils, including helical coils wrapped around a ferrous core, may be used, too. The helical coil may be arranged to have its axis perpendicular to the plane of the substrate, or it may be disposed on its "side" with its axis arranged substantially parallel to the plane of the substrate.

FIG. 5 is a cross-section of the device 10 shown in FIG. 1, provided to show the emitter 18 disposed between the substrate 12 and the top cover 14. To maximize field strength and size, the coil comprising the emitter 18 is preferably as large as the construction will allow. To this end, and although not illustrated, the emitter may occupy the same footprint as the compartment in which it is contained between the substrate 12 and the top cover 14, with the other components being carried on top of the emitter.

Also illustrated in FIG. 5 is a removable backing 26, concealing the adhesive 16 from the atmosphere. The backing 26 is removed to expose the adhesive, which allows the user to apply the device to his skin. The backing 26 may be shaped and sized generally to conform to the shape and size of the adhesive, or it may cover the entirety of the bottom of the substrate. The controller 20 and power source 22 also are schematically illustrated in FIG. 5.

The device 10 is embodied as a wearable device for use in close proximity to an injury, such as an open wound. Accordingly, the device 10 described above may be a disposable device for a single use by the user. However, because of the cost associated with the components, it is likely more desirable that the components encapsulated between the substrate 12 and the top cover 14 are reusable. FIGS. 6-9 embody reusable designs.

Figure 6:
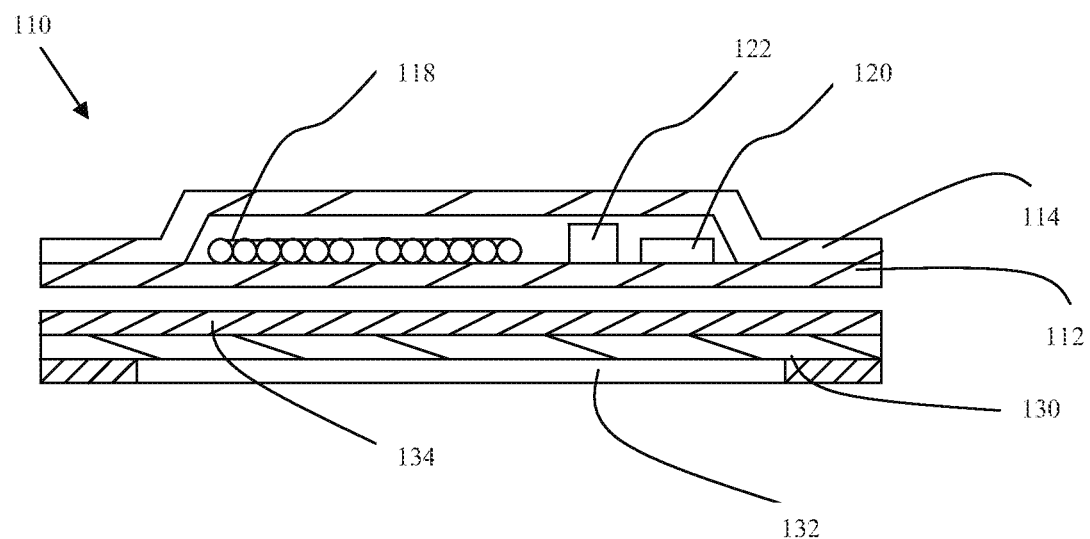
FIG. 6 is a partially-exploded cross-sectional view of a wound healing device according to another embodiment of the invention.

In FIG. 6, a device 110 is similar to the device 10 described above in that it includes a substrate 112 and top cover 114 encapsulating an emitter 118, a controller 120, and a power source 122. The device 110 further includes a disposable substrate 130 to which the substrate is attached and from which it is removed. To this end, the disposable substrate 130 includes an adhesive 132 on its bottom, which preferably is arranged similar to the adhesive 16 in FIG. 3. The disposable substrate 130 preferably also includes a top adhesive 134 to which the substrate 112 can be adhered. Although not shown, the bottom adhesive 132 and the top adhesive 134 may also be covered with a removable backing, like the removable backing 24 described above.

In use, if backings are provided, the backing covering the bottom adhesive 132 is removed from the disposable substrate and the disposable substrate 130 is applied to the user's skin with the adhesive 132 circumscribing the injury. The top adhesive 134 is then exposed (with any backing removed, as necessary). The substrate 112 is thereafter placed on the exposed adhesive 134, to affix the entire device 110 to the user's skin. The device 110 is removed, for example, to charge the power source, to clean the wound, or because the wound has healed, by pulling the entire device off the skin. The disposable substrate 130, with the top and bottom adhesives 132, 134, is then removed from the substrate 112 and discarded. Additional disposable substrates 130 are then provided to reapply the device 110.

In the embodiment of FIG. 6, the substrate 112 preferably is amenable to adhering and being readily removed from the top adhesive 134. According to the embodiment of FIG. 6, the disposable substrate 130, with both accompanying adhesives 132, 134, is disposed of after use. Thus, there is no requirement for the adhesive to be reused, so there is no concern that the adhesive will lose its effectiveness over time.

Figure 7:
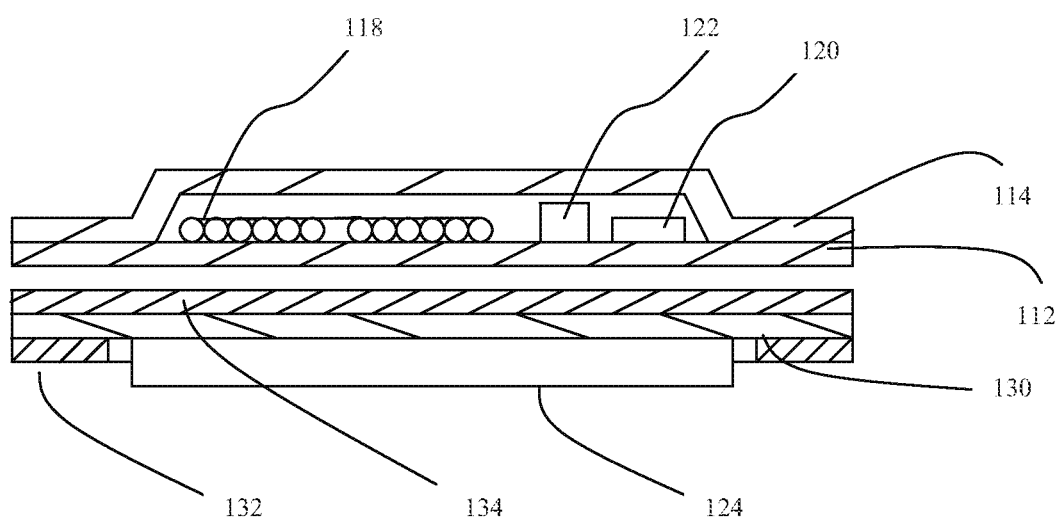
FIG. 7 is a partially-exploded cross-sectional view of a wound healing device according to another embodiment of the invention.

The embodiment of FIG. 7 is similar to the embodiment of FIG. 6, but further includes a pad 124 arranged on the bottom of the disposable substrate 130. The pad is preferably substantially the same as the pad 24 described above and shown in FIG. 4. In this embodiment, the pad 124 may be removed and replaced with greater frequency than the disposable substrate 130.

In another embodiment of the invention, the device could include just the emitter (and any associated power source and controls) carried on a substrate, with or without the top cover. In this embodiment the emitter would preferably be encapsulated or otherwise shielded from the environment, but no top cover would be used. In another embodiment, the adhesive is not provided on the substrate. Instead, the device is applied by the user, for example, by fixing the device with medical tape or adhesive along its edges, that is, the adhesive is not pre-applied. Other known devices could alternatively be applied over the device, such as a cuff, a sleeve or a wrap to hold it in place.

Figure 8:
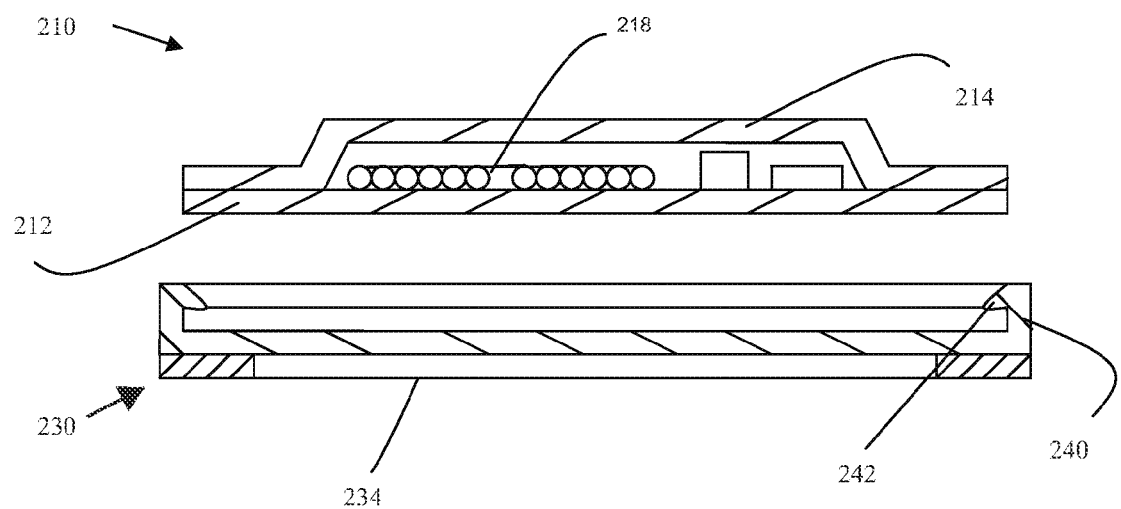
FIG. 8 is a partially-exploded cross-sectional view of a wound healing device according to another embodiment of the invention.
Figure 9:
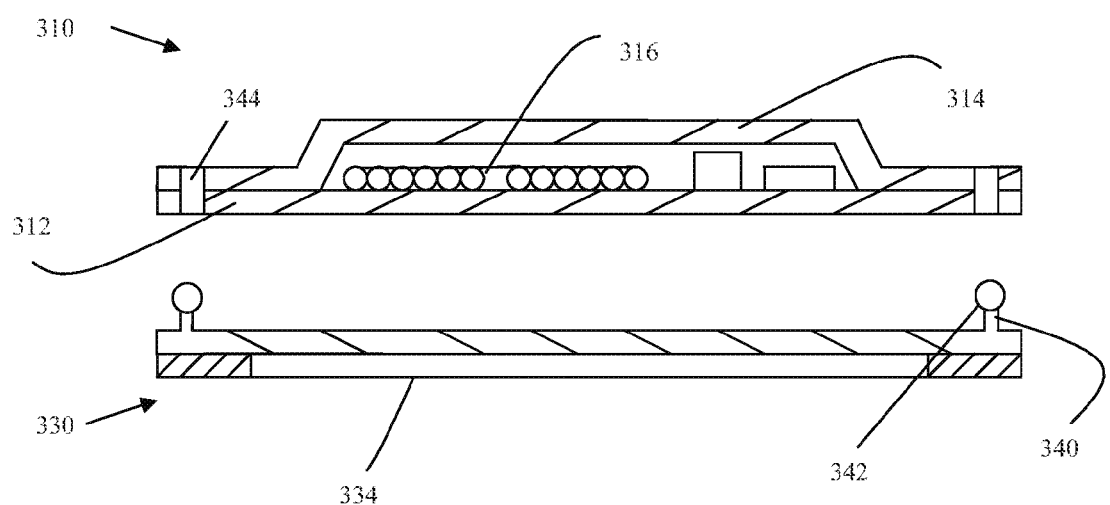
FIG. 9 is a partially-exploded cross-sectional view of a wound healing device according to another embodiment of the invention.

FIG. 8 illustrates yet another embodiment of the invention. There, a device 210 includes a substrate 212 and a top cover 214 forming a compartment housing an emitter 218, similar to the embodiments described above. The device 210 is detachably affixed to a base 230. The base 230 has a bottom adhesive 234 as in the embodiments of FIGS. 6 and 7, but the top of the base 230 and the bottom surface of the substrate 212 are designed to cooperate to maintain the device 210 on the base 230. In the illustrated example, the base 230 defines a peripheral lip 240 extending upwardly about the base 230 and terminating at a retention pawl 242. The substrate 212 has a size and profile adapted to cooperate with the lip 240. More specifically, the substrate 212 can be press fit in to the base 230, such that the peripheral lip 240 retains the substrate 212 therein. As the substrate 212 is pressed into the base 230, the lip 240 will sufficiently deform outwardly until the substrate 212 passes the lip, at which time the lip will return to its normal position, with the pawl 242 overhanging the substrate to retain the substrate in the base 230. When the base 230 is soiled or the device 210 is to otherwise be removed, the entire system, i.e., the device 210 and base 230, may be removed from the user's skin, with the two then being separated, and the base being disposed of.

Although the embodiment of FIG. 8 contemplates a press fit between the device 210 and the base 230, those of skill in the art will readily understand that other selective attachment means may be used to secure the device to the base. For example, fasteners may be used. In one embodiment, illustrated in FIG. 9, a base 330 is provided with an adhesive 334 and posts 340 that extend up from the user's skin. The device 310, including a substrate 312, a top cover 314, and an emitter 316 includes mating apertures 344 that will receive the posts 340. In the illustrated embodiment, the posts 340 include a bulbous top 342, and the mating apertures are sized to be press fit over the bulbous tops 342 of the posts 340. In another embodiment, the posts could be threaded and a nut is threaded onto the posts to retain the device on the base.

In still other embodiments of the invention, a device including an emitter like those described above may be carried by a cuff or strap which will hold the emitter on a user's appendage. The cuff may be fabricated as an orthopedic cuff, such as those conventionally used to treat sprains or the like. The emitter preferably is carried in a compartment of the cuff.

Modifications to the invention will be appreciated by those of ordinary skill in the art. For example, similar to the embodiment of FIGS. 6 and 7, the disposable substrate may consist of a two-sided adhesive tape that is placed on the skin, and to which the substrate 112 is adhered.

In other alternative embodiments, the adhesive may not be used at all. A suction mechanism may be provided to stabilize the device over the wound instead. In this embodiment, a port or the like may be provided through the top of the substrate via which vacuum may be applied through the device. Suction cups, ports or the like are then disposed on the bottom of the substrate, preferably proximate the periphery of the substrate, to maintain the device on the intact skin. Suction could also be used to create a vacuum around the wound to clear discharge from the wound.

Moreover, and as noted above, although the device 110 is illustrated as being generally rectangular in shape, such is not required. Any shape that will facilitate treatment of an injury will suffice. As the footprint of the device increases, the size and number of coils disposed in the device also may increase. The device could be large enough to comprise a wrap that extends substantially entirely around a user's appendage, such as the user's arm or leg.

A number of arrangements of electromagnetic field emitters, signal generating electronics, i.e., to instruct energizing of the coil, and power sources, which provide power for energizing the coil, will be appreciated from this disclosure. In a relatively simple embodiment, a battery, as the power source, the signal generating electronics, and a wire coil are provided on a substrate that is adhered to a patient. The signal generating electronics will include pre-programmed operational sequences as treatment routines that will energize the coil as desired. The components may be encapsulated if desired. This is especially useful if the components are to be reused.

In addition to a battery, signal generating electronics and a magnetic coil, the device may further include a receiver and a transmitter, allowing the device to communicate with an external device. Such an arrangement would allow for downloading to the device signal patterns and schedules, e.g., for specific treatments, as well as updates, and for receiving information from the device, for example, about the treatment, such as accumulated dosimetry and/or other treatment characteristics.

In yet another embodiment of the invention, to assist in providing useful information about the device, the device may further include sensory coils. Such coils could be provided in a device that is substantially the same as device 10, but that is placed on the body spaced from the electromagnetic field emitters to receive the generated magnetic field at a known distance from the generating coil. The receiver coil is placed at a position, such as a position spaced along the device away from the emitter or an opposite side of the injury to be treated, to measure the magnitude and duration of the generated magnetic field. For example, when the device 10 is placed on the top of a user's arm, a device containing the sensory coils may be provided on the bottom, or opposite side, of the user's arm. Using the aforementioned transmitter, the results measured by the sensor coil are then forwarded to a device for interpretation by a physician or technician. The sensory coil may be provided in a low-profile form, such as on a substrate, for application to the user's skin.

In some applications it may be impractical to use a conventional battery, for example, because the battery may not last long enough. When chronic pain is being treated using a device according to the invention, it is preferable that the device function as long as the patient requires. The device may thus instead include a rechargeable power source, such as a rechargeable battery that can be recharged in a conventional manner, such as by being connected, e.g., by a cord or a dock, to a power supply. Alternatively, the device may include an inductively rechargeable power source, such as that described above. In this embodiment, an induction coil is provided on the substrate and an induction device is used external to the device to charge the device. The induction may take any known form including being provided in a wearable device, such as a cuff, that could charge the device, for example, when the user is sleeping.

Figure 10:
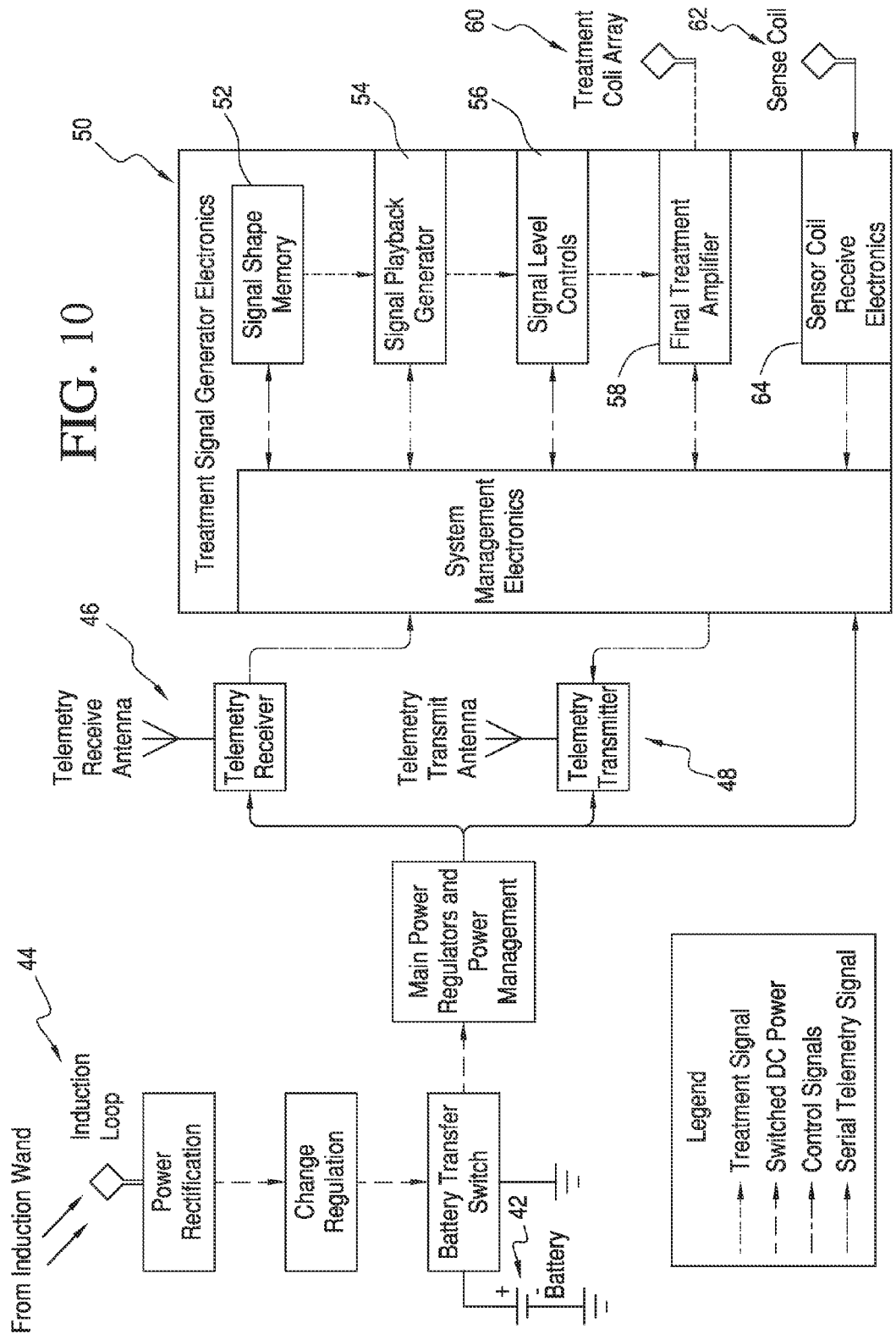
FIG. 10 is a schematic diagram of an induction loop design for use with embodiments of the invention.

FIG. 10 illustrates a schematic of a system according to the invention. There, a battery 42 is the power source, and an induction loop 44 and associated components, such as a rectifier, not shown, are provided to charge the battery 42. A receiver 46 and transmitter 48 are also illustrated, for example, to communicate with a controller disposed outside the device, such as a controller that may be manipulated and/or viewed by a technician to receive information from and send instructions to the device. An example of a signal generator 50 also is illustrated, which will control the coil to provide the treatment routine. The signal generator 50 is illustrated as including a signal shape memory 52, which stores one or more signal shapes used to drive the coil 60; a signal playback generator 54; signal level controls 56; and final treatment amplifier 58. These components all are connected to the treatment coil 60. The schematic also shows a sensor coil 62, such as that described above, and controls 64 for receiving information from the sensor coil 62. This schematic is provided merely as an example; other systems and configurations will be apparent to those of ordinary skill in the art upon being educated by this disclosure.

Figure 11:
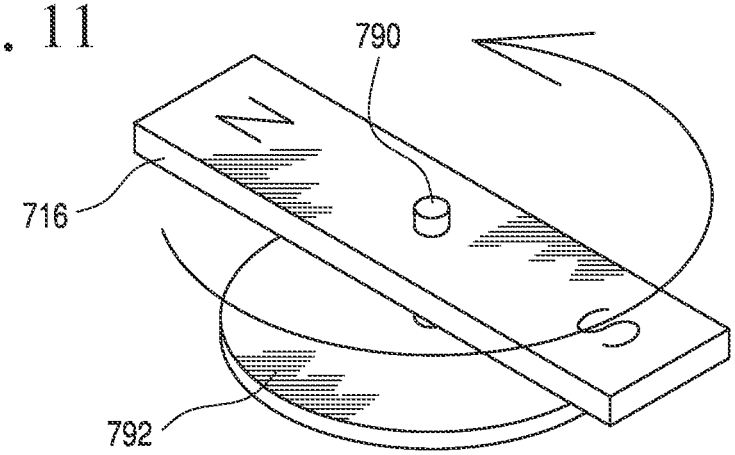
FIG. 11 is a perspective view of a magnetic field generator according to an alternative embodiment of the invention.

The invention has been generally described herein as utilizing a coil as an electromagnetic field emitter. Other embodiments may include different field generators and emitters. For example, an alternative embodiment may include a permanent magnet or combination of magnets, having known field strength and shape. The magnet(s) could then be vibrated, rotated or otherwise moved separately, or together to modulate the field, to create the desired bioeffect. FIG. 11 shows an example of this. There, a permanent magnet 716 generates a magnetic field having a known strength and shape. The magnet 716 is disposed on a shaft 790, rotatable by a rotary actuator 792, such as a piezoelectric actuator. By rotating the magnet, the magnet's field is modulated, which modulation may be optimized for treatment of a broken bone or wound. Thus, the actuator/permanent magnet combination forms a controllable magnetic field emitter. Although not illustrated, the actuator/permanent magnet field emitter will be carried on the substrate, under the top cover sheet.

Although a rotary actuator is illustrated in FIG. 11, this is merely for illustrative and exemplary purposes. In an alternative embodiment, the magnet or magnets could be provided on a linear actuator, such as a piezoelectric actuator, disposed to move along an axial direction. By actuating the actuator, an injury could be selectively disposed in and spaced from the magnet's field. A signal generator for driving the actuator also may be provided. In accordance with another embodiment, a plurality of magnets may be used, one or more of the magnets being rotated or vibrated periodically so that the field produced by the combination of magnets creates the desired therapeutic effect.

While the invention has been described in connection with several presently preferred embodiments thereof, those skilled in the art will appreciate that many modifications and changes may be made therein without departing from the true spirit and scope of the invention which accordingly is intended to be defined solely by the appended claims.

The invention claimed is:

1. A wearable healing device comprising:
   a substrate;
   a magnetic field emitter disposed on a first side of the substrate;
   a medical-grade adhesive on a second, opposite side of the substrate for retaining the substrate on a user's skin;
   a power source powering the magnetic field emitter disposed on the substrate; and
   a controller controlling a magnetic field emitted by the magnetic field emitter;
   further comprising a top cover disposed over the magnetic field emitter and wherein the top cover is fixed to the substrate about a periphery of the magnetic field emitter;
   wherein the magnetic field emitter comprises at least one permanent magnet and a rotary or linear piezoelectric actuator, and the rotary or linear piezoelectric actuator is driven by a signal generator to actuate the at least one permanent magnet to modulate the magnet's field.

2. The healing device of claim 1, wherein the controller modulates the magnetic field emitted by the magnetic field emitter.

3. The healing device of claim 2, wherein the power source is a battery.

4. The healing device of claim 2, wherein the power source is an inductively rechargeable battery and the device further comprises an induction coil which recharges the battery when the device is placed in proximity to a field generator generating a field that will inductively charge the device.

5. The healing device of claim 4, wherein the field generated by the field generator is different from the magnetic field generated by the magnetic field emitter.

6. The healing device of claim 1, further comprising a removable backing applied over the adhesive.

7. The healing device of claim 1, wherein the substrate is flexible.

8. The healing device of claim 7, wherein the magnetic field emitter is affixed to the substrate.

9. The healing device of claim 1, wherein the substrate is non-ferrous.

10. The healing device of claim 1, wherein the adhesive is formed on the substrate.

11. The healing device of claim 1, wherein the magnetic field emitter emits a field of less than about 1000 Gauss.

12. The healing device of claim 1, further comprising a sensory coil spaced from the magnetic field emitter at a known distance to receive the magnetic field generated by the magnetic field emitter.

13. A wearable healing device comprising:
    a substrate;
    a magnetic field emitter disposed on a first side of the substrate;
    a medical-grade adhesive for retaining the substrate on a user's skin;
    a power source powering the magnetic field emitter disposed on the substrate; and
    a controller controlling a magnetic field emitted by the magnetic field emitter;
    wherein the magnetic field emitter comprises at least one permanent magnet and a rotary or linear actuator, and the rotary or linear actuator is driven by a signal generator to actuate the at least one permanent magnet to modulate the magnet's field, wherein the magnetic field emitter comprises a plurality of permanent magnets actuated relative to each other.

14. The healing device of claim 13, further comprising a disposable substrate having a medical-grade adhesive on a first side of the disposable substrate for adhering the disposable substrate to a user's epidermis and an adhesive on a second side of the disposable substrate, opposite the first side, for adhering the disposable substrate to the substrate on which the magnetic field emitter is disposed.

15. The healing device of claim 14, wherein the medical-grade adhesive on the first side of the disposable substrate extends substantially about a perimeter of the disposable substrate.

16. The healing device of claim 14, further comprising a pad disposed on a region of the first side of the disposable substrate circumscribed by the medical-grade adhesive on the first side of the disposable substrate.

17. A wearable healing device comprising:
    a substrate;
    a magnetic field emitter disposed on a first side of the substrate;
    a medical-grade adhesive for retaining the substrate on a user's skin;
    a power source powering the magnetic field emitter disposed on the substrate; and
    a controller controlling a magnetic field emitted by the magnetic field emitter;
    wherein the magnetic field emitter comprises at least one permanent magnet and a linear actuator, and the linear actuator is driven by a signal generator to actuate the at least one permanent magnet to modulate the magnet's field.

* * * * *